United States Patent [19]

Hadary

[11] Patent Number: 4,832,750
[45] Date of Patent: May 23, 1989

[54] TOOTHPICK HOLDER

[76] Inventor: Joseph Hadary, 5405 Linden Ct., Bethesda, Md. 20814

[21] Appl. No.: 127,153

[22] Filed: Dec. 1, 1987

[51] Int. Cl.[4] ............................................ A61C 15/00
[52] U.S. Cl. ................................................... 132/328
[58] Field of Search ....................... 132/89, 90, 93, 91; 433/147

[56] References Cited

U.S. PATENT DOCUMENTS

| | | | |
|---|---|---|---|
| 3,660,902 | 5/1972 | Axelsson | 132/89 |
| 3,892,040 | 7/1975 | Marquis | 132/89 |
| 4,397,327 | 8/1983 | Hadary | 132/89 |
| 4,520,833 | 6/1985 | Hadary | 132/90 |
| 4,564,035 | 1/1986 | Turner | 132/90 |
| 4,630,623 | 12/1986 | Hadary | 132/89 |
| 4,672,986 | 6/1987 | Hadary | 132/89 |

FOREIGN PATENT DOCUMENTS

| | | | |
|---|---|---|---|
| 380150 | 9/1923 | Fed. Rep. of Germany | 132/90 |
| 2842405 | 4/1980 | Fed. Rep. of Germany | 132/89 |
| 82/01126 | 4/1982 | World Int. Prop. O. | 132/89 |
| 872511 | 7/1961 | United Kingdom | 132/89 |

Primary Examiner—Robert Peshock
Attorney, Agent, or Firm—Dennis H. Lambert

[57] ABSTRACT

A toothpick holder for holding toothpicks in different positions to facilitate access to different portions of the dental arches. The holder includes a handle with an arm thereon having a toothpick receiving opening through which a toothpick can be positioned to point first in one direction and also in a direction 180 degrees opposite the first position for gaining access to the fronts and backs of all the interdental, or proximal spaces.

1 Claim, 1 Drawing Sheet

TOOTHPICK HOLDER

BACKGROUND OF THE INVENTION

1. Field of the Invention:

This invention relates to dental implements, and more particularly, to a toothpick holder for holding toothpicks in a plurality of positions for easier access to all areas of the dental arches.

2. Prior Art:

It is well known by the dental profession that brushing alone does not adequately clean the sides of the teeth forming the interdental spaces. Thus, flossing and other cleaning methods are recommended in conjunction with brushing. Moreover, the proper use of toothpicks, and in particular triangularly-shaped toothpicks which conform to the contours of the interdental spaces, can be particularly effective in cleaning the spaces between the teeth.

However, except for a few attempts at developing a toothpick holder, people are generally limited to the use of wood or plastic toothpicks held in the user's hand. Accordingly, the use of a toothpick is only partially effective inasmuch as a hand-held toothpick cannot be inserted into the interdental spaces from the back of the teeth, and these areas are usually not cleaned.

Examples of prior art toothpick holders are shown in U.S. Pat. No. 4,397,327 and 4,630,623. U.S. Pat. No. 4,397,327 teaches a toothpick holder capable of holding a toothpick having a wedge-shaped cross-section in any one of several different adjusted latched positions wherein the holder properly orients such a toothpick for optimum effectiveness in all areas of the mouth. However, as set forth more fully hereinafter, the present invention provides for the proper orientation of wedge-shaped toothpicks without resorting to a latching mechanism. U.S. Pat. No. 4,630,623 discloses a holder with multiple arms, whereas the present invention teaches a toothpick holder for orienting toothpicks having wedge-shaped cross-sections in opposite directions with only one arm.

SUMMARY OF THE INVENTION

It is, therefore, a primary object of this invention to provide a toothpick holder which is economical and simple in construction and which securely holds toothpicks in a plurality of orientations to facilitate access to different areas of the teeth.

Another object of the invention is to provide a toothpick holder having a shaped opening at one end of the handle for holding first one toothpick in a predetermined orientation and then another toothpick in a predetermined and opposite orientation.

A more specific object of the invention is to provide a toothpick holder for holding a toothpick having a wedge-shaped cross-section such that a toothpick may be inserted into a shaped opening with a toothpick being properly oriented for one side of the mouth or the other, depending upon which side of the opening the toothpick is inserted into.

These and other objects of the invention are accomplished by an elongate handle with an angularly outwardly extending arm at one end in which a shaped opening is formed for holding a toothpick in one of two predetermined directions to facilitate access to the interdental spaces at different sides of the mouth. The holder is of one-piece construction and provides in one implement, without the necessity of manipulating clamps, adjustments, etc., a simple and inexpensive tool for holding toothpicks in a plurality of orientations.

BRIEF DESCRIPTION OF THE DRAWINGS

Other objects of this invention will appear in the following description and appended claims, reference being made to the accompanying drawings forming a part of the specification, and wherein like reference numerals designate like parts throughout the several views.

DESCRIPTION OF THE PREFERRED EMBODIMENTS

Figure 1:
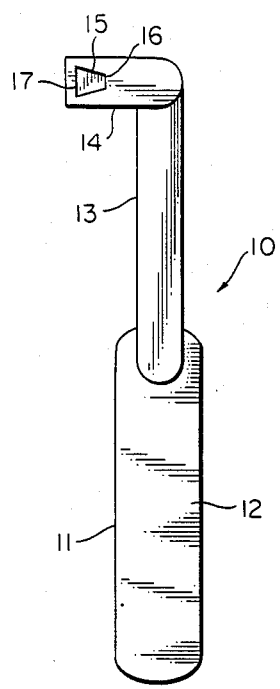
FIG. 1 is a front view in elevation of the holder in accordance with the invention.
Figure 2:
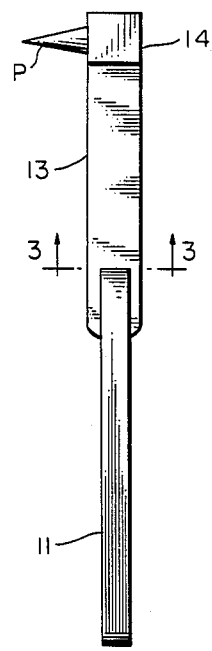
FIG. 2 is a side view in elevation of the toothpick holder of FIG. 1.
Figure 3:
FIG. 3 is transverse sectional view taken along line 3-3 of FIG. 2.
Figure 4:
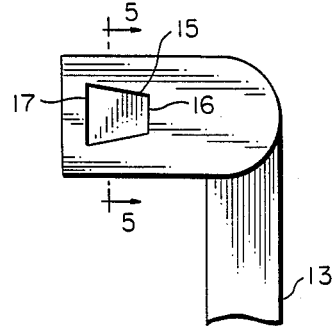
FIG. 4 is an enlarged, fragmentary front elevational view of the holder of FIG. 1.
Figure 5:
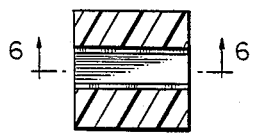
FIG. 5 is a transverse sectional view taken along line 5-5 of FIG. 4.
Figure 7:
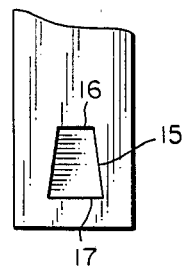
FIG. 7 is a fragmentary view in elevation taken along line 7-7 of FIG. 6.

Referring more specifically to the drawings, a holder in accordance with the invention is indicated generally at 10 and comprises an elongate handle 11 having a relatively flat portion 12 extending over slightly half of the total length of the handle, and ending with a stem 13. Projecting at a right angle from the stem, whose cross-section is shown in FIG. 3, is an arm 14. The arm, which projects outwardly at a right angle from the connection with the stem 13 has a trapeziodably-shaped opening 15 extending completely therethrough and of constant cross-section. The top 16 of the opening is directed toward the stem and the base, or bottom 17 of the opening 15 is disposed toward the free end of the arm, as shown in FIG. 7.

Figure 6:
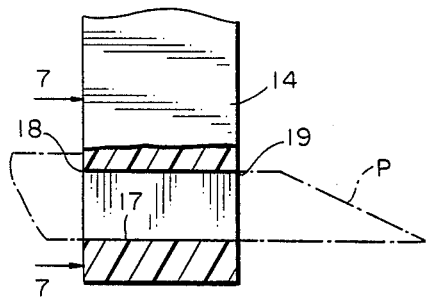
FIG. 6 is an enlarged sectional view taken along line 6-6 of FIG. 5.
Figure 8:
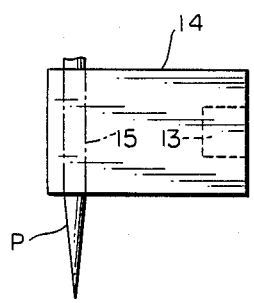
FIG. 8 is an enlarged top or end view of the holder with a toothpick in one of two possible orientations.
Figure 9:
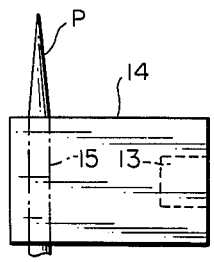
FIG. 9 is an enlarged top or end view of the holder with a toothpick oriented in opposition to the toothpick of FIG. 8.

A toothpick P inserted into opening 15 can be oriented in two directions as shown in FIGS. 8 and 9. As seen best in FIG. 6, when a wood toothpick having a wedge-shaped cross-section is inserted with its flat bottom parallel to the bottom 17 of opening 15, a portion of the toothpick's apex engages shoulder 18 and is shaved, rolled back, or compressed, depending on the moisture content and hardness of the toothpick, tending to wedge the toothpick in place with approximately, ½ inch of the pointed end projecting outwardly from the arm 14. Inserting the toothpick into the same opening but from an opposite side of the opening, shoulder 19 engages the toothpick in the same way as the shoulder at 18 does and tends to wedge the toothpick with its pointed end in an opposite orientation.

The toothpicks may comprise any one of a variety of interdental cleaners that are commonly available, such as the brand sold under the trademark STIM-U-DENT, by Johnson and Johnson. In use, the pointed end of the toothpicks are fully inserted into opening 15 of the holder/and the unused portions projecting rearwardly are broken off and discarded.

The toothpick holder of the invention thus properly orients toothpicks having a wedge shape in cross-section for access to all interstices of the teeth from both the cheek and tongue sides of the teeth.

The holder may be manufactured from any suitable material, such as injection molded plastic. In its present form, the holder has an overall length of about five inches, and the arm 14 is about 7/16 inch long, with the base of the opening 15 being spaced about 1/16 inch from the free outer end of the arm.

While the holder has been shown and described in detail, it is obvious that the invention is not to be limited to the exact form disclosed, and that changes in detail and construction may be made therein within the scope of the invention, without departing from the spirit thereof.

Having set forth and disclosed the nature of this invention,

What is claimed is:

1. In a toothpick holder for selectively holding toothpicks in one of two predetermined orientations, wherein the toothpick holder comprises an elongate handle having an arm projecting from one end of the handle at a right angle to the longitudinal axis of the handle, and said arm has a free end with an opening extending completely transversely therethrough for gripping and holding a toothpick inserted through the opening, the improvement comprising:

a single arm projecting from the handle; and said opening having a trapezoidal configuration in transverse cross-section, with a uniform size and shape throughout its length and with the base of the trapezoidal opening lying parallel to the axis of the handle, whereby a toothpick having a wedge-shaped transverse cross-section may be inserted into the opening from either end of the opening, with the apex of the opening engaging and compressing the narrower edge of the toothpick to securely wedge the toothpick in place in the opening for orientation of the toothpick in either of two desired directions.

* * * * *